United States Patent [19]

Metz et al.

[11] 4,294,851
[45] * Oct. 13, 1981

[54] AMINOBENZOIC ACID DERIVATIVES

[76] Inventors: Gunter Metz, Auf dem Rucken 29; Manfred Specker, Weilerhalde 32, both of Blaubeuren, Fed. Rep. of Germany

[*] Notice: The portion of the term of this patent subsequent to Mar. 27, 1996, has been disclaimed.

[21] Appl. No.: 919,747

[22] Filed: Jun. 27, 1978

[30] Foreign Application Priority Data

Jul. 4, 1977 [DE] Fed. Rep. of Germany ....... 2730174

[51] Int. Cl.³ .................. A61K 31/17; A61K 31/165; C07C 101/00; C07C 103/78
[52] U.S. Cl. .................................... 424/311; 424/250; 424/251; 424/263; 424/267; 424/274; 424/303; 424/324; 544/284; 544/287; 544/391; 260/326.47; 546/337; 546/233
[58] Field of Search ...................... 260/559 R, 559 A; 424/324, 311; 464/157

[56] References Cited

U.S. PATENT DOCUMENTS

| | | | |
|---|---|---|---|
| 3,719,687 | 3/1973 | Mendel et al. | 260/559 R |
| 3,840,598 | 10/1974 | Lesher | 260/559 R |
| 4,021,481 | 5/1977 | Almer et al. | 260/559 A |
| 4,059,621 | 11/1977 | Vincent et al. | 260/559 A |
| 4,070,485 | 1/1978 | Malen et al. | 260/559 A |
| 4,146,637 | 3/1979 | Metz et al. | 260/559 A |

OTHER PUBLICATIONS

Metz, et al., "Chemical Abstracts", vol. 88, 1978, col. 89399z.

*Primary Examiner*—Donald G. Davis
*Assistant Examiner*—James H. Turnipseed
*Attorney, Agent, or Firm*—Michael N. Meller

[57] ABSTRACT

The object of the present invention are novel aminobenzoic acid derivatives having the general formula:

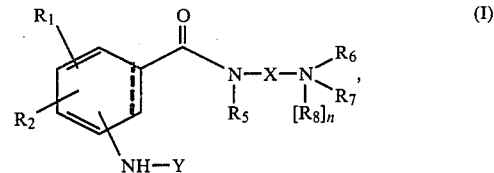

wherein
$R_1$ is hydrogen, chlorine, hydroxy, acetoxy or $C_1$–$C_3$-alkoxy;
$R_2$ is hydrogen, chlorine or sulfamoyl;
$R_5$ is hydrogen or combined with $R_6$ a $C_2$–$C_3$-alkylene;
Y is the group

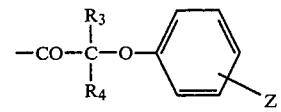

or in ortho-position together with the hydrogen atom on the nitrogen and with $R_5$ the group

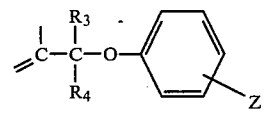

wherein
$R_3$ is hydrogen or methyl;
$R_4$ is hydrogen, $C_1$–$C_3$-alkyl, or with Z substituted phenoxy; and
Z is hydrogen, halogen or trifluoromethyl;
X is $C_1$–$C_3$-alkylene forming, if necessary, under substitution with $R_6$ a 5- or 6-link aliphatic or aromatic ring system;
$R_6$ is $C_1$–$C_4$-alkyl or in combination with X a $C_3$–$C_4$-cycloalkylene or cycloarylene;
$R_7$ is hydrogen, $C_1$–$C_3$-alkyl, formyl, the group Y, or together with $R_6$ a $C_4$–$C_5$-cycloalkylene, or together with X and $R_6$ pyridylmethyl;
$R_8$ is hydrogen or, if necessary, halogen- or phenyl-substituted $C_1$–$C_4$-alkyl or $C_1$–$C_4$-alkenyl; and
n has the value 0 or 1,
and if n=1, their salts with pharmaceutically compatible acid radicals.

Said compounds show antilipemic activity.

The present invention relates furthermore to the preparation of said compounds and of drugs containing such compounds.

2 Claims, No Drawings

AMINOBENZOIC ACID DERIVATIVES

The object of the present invention are novel aminobenzoic acid derivatives having the general formula:

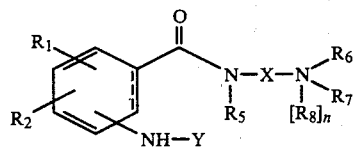
(I)

wherein:
$R_1$ is hydrogen, chlorine, hydroxy, acetoxy or $C_1$–$C_3$ alkoxy,
$R_2$ is hydrogen, chlorine or sulfamoyl,
$R_5$ is hydrogen or combined with $R_6$ a $C_2$–$C_3$-alkylene,
Y is the group:

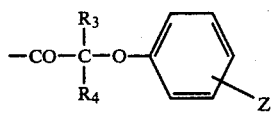

or in ortho-position together with the hydrogen atom on the nitrogen and with $R_5$ the group:

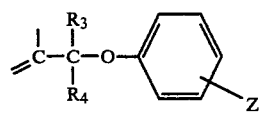

wherein:
$R_3$ is hydrogen or methyl,
$R_4$ is hydrogen, $C_1$–$C_3$alkyl or with Z-substituted phenoxy, and
Z is hydrogen, halogen or trifluoromethyl,
X is $C_1$–$C_3$-alkylene forming, if necessary, with $R_6$-substitution a 5- or 6-link aliphatic or aromatic ring system,
$R_6$ is $C_1$–$C_4$-alkyl or in combination with X a $C_3$–$C_4$-cycloalkylene or cycloarylene,
$R_7$ is hydrogen, $C_1$–$C_3$-alkyl, formyl, the group Y or together with $R_6$ a $C_4$–$C_5$-cycloalkylene, or together with X and $R_6$ pyridylmethyl,
$R_8$ is hydrogen or, if necessary, halogen- or phenyl-substituted $C_1$–$C_4$-alkyl or $C_1$–$C_4$-alkenyl, and
n has the value of 0 or 1,
and, if n=1, their salts with pharmaceutically compatible acid esters.

This includes the aminobenzoic acid derivatives having the general formula II:

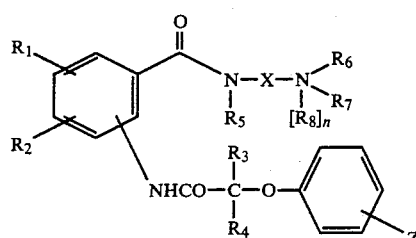
(II)

wherein $R_1$, $R_2$, $R_3$, $R_4$, $R_5$, Z, X, $R_6$, $R_7$, $R_8$ and n have the meaning as defined above.

The object of the present invention are furthermore the aminobenzoic acid derivatives formed by ring closure with an —NHY—group of general formula (I) in the o-position and having the general formula III:

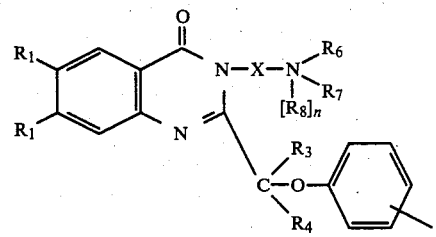
(III)

wherein $R_1$, $R_2$, $R_3$, $R_4$, Z, X, $R_6$, $R_7$, $R_8$ and n have the meaning defined above, with the proviso that at least one of the radicals $R_3$ or $R_4$ is a hydrogen atom.

The halogen atoms in radical Z may be fluorine, chlorine, bromine and iodine atoms, preferably chlorine and fluorine atoms. Preferred are the p- and o-positions, especially the p-position. The trifluoromethyl group is preferably in the m-position.

Examples of suitable alkyl radicals are the methyl, ethyl, propyl, isopropyl, n-butyl and the tert. butyl groups. If $R_8$ is a halogen alkyl radical, the methoiodide, ethoiodide, butylbromide- and phenylpropenylbromide radicals are preferred.

The present invention relates furthermore to a method of producing the aminobenzoic acid derivatives having the general formula (I), said method being characterized by reacting a carboxylic acid having the general formula:

Y—OH     (IV), wherein Y is as defined above, or a reactive derivative of said carboxylic acid with an aminobenzoic acid of the general formula:

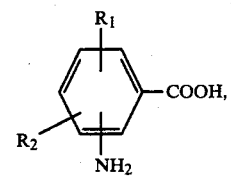
(V)

wherein $R_1$ and $R_2$ are as defined above, or with its reactive derivatives, and by reacting the resulting aminobenzoic acid of the general formula:

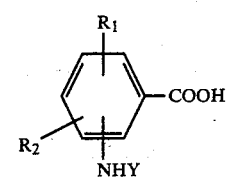
(VI)

or its reactive derivative with a diamine of the general formula:

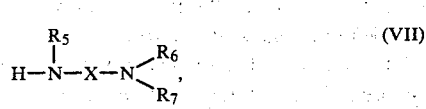

wherein $R_5$, $R_6$, $R_7$ and X are as defined above, and by subsequently introducing, if necessary, in a manner known per se the $R_8$-group as defined above, so as to prepare a quarternary ammonium compound.

A further method comprises reacting the aminobenzoic acid of general formula (V) or its reactive derivative first with the diamine of the general formula (VII), usefully with the addition of a formyl or acetyl radical as protective group for the $NH_2$-radical, and upon removal of said protective group with the carboxylic acid of formula (IV) or with its reactive derivative.

If group —NH—Y is in the o-position in general formula (I), the method is usefully modified by reacting, in a suitable solvent, isatoic acid anhydride as reactive derivative of the aminobenzoic acid of general formula (V), if necessary substituted with $R_1$ and $R_2$, with the diamine of general formula (VII), and by reacting the resulting aminobenzoic acid derivative having the general formula:

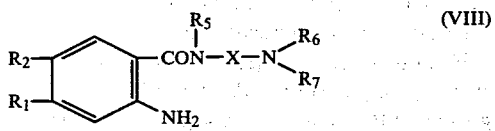

with the carboxylic acid having the general formula (IV), or with its reactive derivative.

Suitable acid derivatives are, for example, acid chlorides, acid anhydrides, esters, as well as the alkyl carboxylic acid esters or alkyl carboxylic acid anhydrides accessible by reacting the carboxyl group with haloformic acid esters.

The direct reaction of the carboxylic acid (IV) with the aminobenzoic acid (V), or the direct reaction of the aminobenzoic acid (VI) with the diamine (VII) is preferably carried out in aromatic hydrocarbons or halogen-hydrocarbons under heating to reflux temperature and with the simultaneous use of water-separating components such as, for example, phosphorus oxychloride, phosphorus trichloride, phosphorus pentachloride, and dicyclohexyl carbodiimide.

The reaction of the acid derivatives with the diamine (VII) is preferably carried out in halogen-hydrocarbons or ethers at room temperature, or under heating up to boiling temperature.

In the reaction of the carboxylic acid with a chloroformic acid ester, the alkyl carboxylic acid anhydride derivative formed is usefully not isolated but directly reacted with the diamine (VII) in a one-step process.

The resulting basic aminobenzoic acid derivatives of the general formula (I) may be converted into their respective salts by reaction with pharmaceutically usable acids such as, for example, haloacids, citric acid, fumaric acid, salicylic acid, nicotinic acid, as well as by reaction with the acids having the general formulas (IV) and (VI), or said derivatives may be quaternized by reaction with alkyl halides.

If the o-position is substituted with the —NH—Y—group, the cyclized aminobenzoic acid derivatives of general formula (III) formally obtained by water separation may be produced by heating the respective aminobenzoic acids in suitable solvents or without solvents, or said derivatives may be obtained directly in the reaction of the aminobenzoic acid of general formula (VI) or of its reactive derivative with the diamine having the general formula (VII). Both methods of preparation are limited to the extent that because of steric hindrance in connection with the cyclized compounds of the general formula (III), at least one of the two radicals $R_3$ and $R_4$ in group Y must be a hydrogen atom.

The compounds according to the invention show in particular excellent antilipemic activity with good compatibility.

The therapeutic effectiveness of the compounds of the present invention according to examples 2, 43, 75, 83 and 86 was tested on female rats against the known antilipaemica 2-(p-chlorophenoxy)-2-methyl-propionic acid (clofibrinic acid), its ethyl ester (clofibrate), as well as against one of the initial compounds of general formula (VI), namely 2-(2-p-chlorophenoxy)-2-methylpropionamido)-benzoic acid. The compounds or the vehicle (1% tragacanth solution), respectively, were administered with the help of a pharyngeal tube over a test period of 14 days; the blood samples for the determination of the serum cholesterol and serum triglyceride levels were drawn 24 hours after the last dose was administered.

The effectiveness on normo-lipemic rats (10 animals per group) with a body weight of 50 to 60 grams was examined in a first test series in which said animals received a standardized, pelletized laboratory diet (normal diet) over the entire test period. The diet essentially consisted of raw proteins and carbohydrates with a raw fat content of 3.9% maximum, enriched by vitamins, mineral substances and amino acids.

The results of this test series are summarized in Table 1. The values of percent change ($\pm\%$) indicated in said table relate in each case to the mean group value (mg %) of the control group which was determined for 20 animals. Also significance p is based on the control values.

TABLE 1

| | Antilipemic Activity with Normal Diet | | |
|---|---|---|---|
| Example | mg/kg | Cholesterol $\pm \%$ | Triglyceride $\pm \%$ |
| 43 | 250 | − 0.33 | − 46.0*** |
| 83 | 250 | + 8.5 | − 16.4* |
| clofibrinic acid | 100 | + 1.1 | − 20.8 |
|  | 250 | − 6.6 | − 26.5* |
| ref. 1 | 100 | + 2.1 | + 0.8 |
|  | 300 | + 0.9 | + 2.9 |

*$p < 0.05$
***$p < 0.001$

The effectiveness on hypercholesteremic rats was examined in a second test in accordance with the instructions by Berger et al, Proc. Soc. Exp. Biol. 132, 253 (1969). For the purpose of achieving an artificial hyperlipemia, the initially normo-lipemic animals received the above-specified normal diet in powdered form admixed with 2% cholesterol and 1% cholic acid. The results of this study are summarized in Table 2; also in this case, the indicated changes are based on the mean group value of the control group.

TABLE 2

Antilipemic Activity with Hypercholesterol Diet

| Example | mg/kg | Cholesterol ± % | Triglyceride ± % |
|---|---|---|---|
| 43 | 250 | − 63.6*** | − 6.7 |
| 75 | 131 | − 35.2* | + 1.5 |
| 2 (HCl) | 279 | − 12.3 | − 6.4 |
| 86 (HCl) | 275 | − 3.5 | − 29.4 |
| clofibrinic acid | 100 | + 6.7 | − 8.2 |
|  | 250 | + 9.5 | − 17.4 |
| clofibrate | 250 | − 3.0 | − 12.5 |
| ref. 1 | 100 | + 3.2 | − 25.7 |
|  | 300 | + 5.0 | + 25.5 |

*$p < 0.05$
***$p < 0.001$

Taking into consideration that the clofibrinic acid radical is the active principle in the tested compounds of the invention with respect to the lipid reduction, and that under the particularly difficult conditions of the hypercholesterol tests, the doses of the compounds according to examples 2, 43 and 86 correspond with a dispensing of 128 mg/kg clofibrinic acid, and the one of the compound according to example 75 even only with 64 mg/kg clofibrinic acid, it follows that the therapeutic index is substantially higher as compared to clofibrinic acid and clofibrate. Suprisingly, however, is the complete inactivity of the tested reference compound of general formula (VI) (Ref.1). In conformity with the results indicated in Table 2, it can be safely assumed that the gradual activity of the compounds is mainly determined by the basic radial according to general formula (VII).

A pharmacological screening of selected compounds of general formulas (II) and (III) showed that in addition to antilipemic activity, said compounds have still other valuable therapeutic properties. For example, the compounds according to examples 14 and 57 retard the aggregation of blood platelets with an activity that is superior to the one of adenosine and acetylsalicylic acid. The compounds according to examples 89, 93 and 94 show in particular antiarrhythmic and cardiotrophic properties, as well as a pronounced β-adrenergic retardation with the same effect of or superior to the known reference compounds such as Practalol or Prinodolol.

The drugs according to the invention contain as effective agent one or a plurality of aminobenzoic acid derivatives of the general formula (I). Said drugs are preferably administered orally, e.g. in the form of tablets or capsules containing, if necessary, the usual pharmaceutical carrier substances and adjuvants such as, for example, lactose, starch, talcum and magnesium stearate. Their pharmaceutically compatible salts are particularly suitable for use in injection solutions.

The compounds according to the invention are administered orally or rectally in daily dosages of from 250 to 1500 mg depending on the specific case, preferably in doses of 500 to 750 mg in the usual pharmaceutical forms, or as injection solution in daily doses of from 50 to 250 mg, preferably 100 to 200 mg.

The preparation of the compounds according to the present invention is described with the help of the following examples:

EXAMPLE 1

13.7 g (0.1 mol) 3-aminobenzoic acid and an addition of 10 g (0.1 mol) triethylamine are suspended in 150 ml chloroform, admixed with 20.5 g (0.1 mol) p-chlorophenoxyacetyl chloride, and heated for 5 hours under reflux. After the mixture has cooled off, the crystals are removed by suction; the yield is 23.3 g (76.5%) 3-(p-chlorophenoxyacetamido)-benzoic acid with a MP of 208° C.

15.24 g (0.05 mol) of said aminobenzoic acid and an addition of 6.4 g (0.055 mol) diethylaminoethylamine are suspended in 100 ml toluene and mixed with 7.7 g (0.05 mol) phosphorus oxychloride. This formulation is subsequently heated for 6 hours under reflux. After cooling off, the solution is agitated with water and made alkaline with diluted soda lye. After the alkaline phase has been separated, the solution is again washed with water. The residue remaining after distilling off the solvent is crystallized from a small amount of diisopropyl ether; the yield is 16.8 g (83.2%) 3-(p-chlorophenoxyacetamido)-N-(2-diethylaminoethyl)-benzamide with a MP of 100° C.

| | | Elementary Analysis: | | |
|---|---|---|---|---|
| | | | C | H | N |
| $C_{21}H_{26}ClN_3O_3$ | (403.9) | Calculated: | 62.43 | 6.49 | 10.40 |
| | | Obtained: | 62.33 | 6.56 | 10.03 |

Hydrochloride, MP 92° C.

EXAMPLE 2

64 g (0.2 mol) 4-(2-(p-chlorophenoxy)-2-methyl-propionamido)benzoic acid with an MP of 191° C. are reacted with 24 g thionylchloride in 200 ml toluene and heated for 6 hours to 100° C. The crystals formed after cooling off are removed by suction, yielding 45 g (66.3%) of the respective acid chloride with an MP of 148° C. 17.8 g (0.052 mol) of this acid chloride are dissolved in 150 ml chlorofom and reacted under heating with 6 g of 1-(2-aminoethyl)-pyrrolidine. The chloroform solution washed with diluted soda lye and water is evaporated, and the residue is crystallized from acetone, yielding 14.5 g (64.3%) 4-(2-(p-chlorophenoxy)-2-methyl-propionamido)-N-(1-ethylpyrrolidinyl-2-methyl)-benzamide with an MP of 180° C.

| | | Elementary Analysis: | | |
|---|---|---|---|---|
| | | | C | H | N |
| $C_{23}H_{28}ClN_3O_3$ | (429.9) | Calculated: | 64.25 | 6.56 | 9.77 |
| | | Obtained: | 64.36 | 6.62 | 9.91 |

Hydrochloride, MP 191° C.

EXAMPLE 3

16.7 g (0.05 mol) 2-(2-(p-chlorophenoxy)-2-methyl-propionamido)benzoic acid of MP 199° C. are suspended in 60 ml toluene and successively admixed with 2.05 g phosphorus trichloride and 5.9 g 2-diethylaminoethyl amine. This formulation is heated under reflux for 5 hours and washed after cooling off with diluted soda lye and water.

After distilling off the solvent, 10 g (42%) of 2-(2-(p-chlorophenoxy)-2-methyl-propionamido)-N-(2-diethylaminoethyl)- benzamide are obtained in the form of oil. The oily residue is dissolved in diisopropyl ether and admixed with isopropanolic hydrochloric acid up to pH 3. The hydrochloride formed thereby is removed by suction and shows upon drying a MP of 149° C. The titration with 0.1 $NHClO_4$ in glacial acetic acid with an addition of mercury acetate yields a content of 102.8%,

EXAMPLE 4

16.3 g (0.1 mol) isatoic acid anhydride are suspended in 100 ml toluene and mixed with 11.6 g (0.1 mol) 2-diethylaminoethylamine. The resulting suspension is agitated for 4 hours, with solution occurring gradually under mild exothermic reaction and separation of $CO_2$. After leaving the solution overnight the filtered solution is rinsed with diluted hydrochloric acid. The aqueous hydrochloric acid phase is made alkaline with NaOH and extracted with chloroform. After evaporation of the solvent, 20.8 g (88.4%) N-(2-diethylaminoethyl)-2-aminobenzamide are obtained in the form of oil.

10 g (0.042 mol) of said amide are reacted in chloroform with 8.6 (0.042 mol) p-chlorophenoxyacetic acid chloride. The chloroform solution is evaporated after washing with diluted soda lye and water, yielding 12.8 g (75.7%) 2-(p-chlorophenoxyacetamido)-N-(2-diethylaminoethyl)-benzamide with a MP of 109° C.

Citrate MP 111° C./maleinate MP 134° C.

EXAMPLE 5

30.6 g (0.2 mol) 5-amino-2-hydroxybenzoic acid are reacted with 41 g (0.2 mol) p-chlorophenozyacetyl chloride using the method according to example 1. Obtained are 62.7 g (97.5%) 5-(p-chlorophenoxyacetamido)-2-hydroxybenzoic acid with MP of 227° C.

The reaction with acetic anhydride yields 5-(-p-chlorophenoxyacetamido)-2-acetylbenzoic acid with a MP of 198° C., or 58.5%.

36.4 g (0.1 mol) of said acetylbenzoic acid are suspended in 200 ml tetrahydrofuran with an addition of 12.0 g (0.12 mol) triethylamine. 13.0 g (0.12 mol) chloroformic acid ethyl ester are added at a temperature in the range of 5° to 10° C.; this preparation is agitated for 3 hours with the cooling stopped after 2 hours. 12.8 g (0.1 mol) 1-ethyl-2-(aminomethyl)-pyrrolidine are added under agitation. After leaving the formulation standing over night, the solvent is largely evaporated under vacuum, and the residue is decomposed with water.

The viscous oil separated in this process is adsorbed with chloroform and rinsed with diluted soda lye and water. The oily residue remaining after evaporation crystallizes from a small amount of diisopropyl ether and yields 24.7 g (52.2%) 5-(p-chlorophenoxyacetamido)-2-acetyl-N-(1-ethylpyrrolidinyl-2-methyl)-benzamide with a MP of 139° C. The content determination by titration with 0.1 N $HClO_4$ in glacial acetic acid shows a content of 103.4%.

EXAMPLE 6

1 g (21 millimol) of the benzamide prepared according to example 5 is heated in aqueous soda lye with an addition of a small amount of ethanol for 15 minutes to about 80° C. and subsequently acidified with diluted hydrochloric acid. Upon extraction with chloroform and removal of the solvent by evaporation, 0.8 g (88.2%) 5-(p-chlorophenoxyacetamido)-2-hydroxy-N-(1-ethylpyrrolidinyl-2-methyl-benzamide hydrochloride with a MP of 112° C. is obtained.

The benzamide obtained from the hydrochloride by treatment with diluted soda lye shows a MP of 87° C.

EXAMPLE 7

4.16 g (0.01 mol) of the compound according to example 89 are dissolved in 30 ml ethanol and admixed with 1.42 g (0.01 mol) methyl iodide. The solution is heated under reflux for 2 hours and subsequently evaporated under vacuum. The residue is crystallized from ethanol with an addition of acetone, with a yield of 5.5 g (98.5%) of the respective methiodine with a MP of 114° C.

EXAMPLE 8

2.75 g (0.005 mol) of the methiodide according to example 7 are dissolved in 20 ml of a mixture of acetone and methanol and admixed with 0.7 g AgCl. The suspension is briefly heated and removed by filtration from the precipitated AgI while still warm. The respective methylchloride crystallizes during cooling and is recrystallized from a small amount of ethanol with an addition of acetone.

Additional compounds were prepared in accordance with the method according to examples 1 to 6, as well as examples 7 and 8 in the case of the quaternary amides. Said additional compounds are included in the following tables together with those prepared in the preceding examples 1 to 8.

| Ex. | $R_1$ | $R_2$ | NH—Y in Position No. | $R_3$ | $R_4$ | Z | $N-X-N\genfrac{}{}{0pt}{}{R_5\ R_6}{R_7}$ | $R_8$ | Acid Radical n=1 | MP °C. |
|---|---|---|---|---|---|---|---|---|---|---|
| 1 | H | H | 3 | H | H | p-Cl | $NHCH_2CH_2N(C_2H_5)_2$ | — | — | 100 |
|   |   |   |   |   |   |   |   | H | Cl | 92 |
| 2 | H | H | 4 | $CH_3$ | $CH_3$ | p-Cl | $NHCH_2CH_2$—N (pyrrolidine) | — | — | 180 |
|   |   |   |   |   |   |   |   | H | Cl | 191 |
| 3 | H | H | 2 | $CH_3$ | $CH_3$ | p-Cl | $NHCH_2CH_2N(C_2H_5)_2$ | — | — | oily |
|   |   |   |   |   |   |   |   | H | Cl | 149 |
| 4 | H | H | 2 | H | H | p-Cl | " | — | — | 109 |
|   |   |   |   |   |   |   |   | H | Citrate | 111 |
|   |   |   |   |   |   |   |   | H | Maleinate | 134 |

-continued

| Ex. | R₁ | R₂ | NH—Y in Position No. | R₃ | R₄ | Z | $\begin{array}{c}R_5\\|\\N-X-N\end{array}\begin{array}{c}R_6\\\\R_7\end{array}$ | R₈ | Acid Radical n=1 | MP °C. |
|---|---|---|---|---|---|---|---|---|---|---|
| 5 | 2-OCOCH₃ | H | 5 | H | H | p-Cl | NHCH₂-pyrrolidine-N-C₂H₅ | — | — | 139 |
| 6 | 2-OH | H | 5 | H | H | p-Cl | " | — | — | 87 |
|   |      |   |   |   |   |      |   | H | Cl | 112 |
| 7 | H | H | 4 | CH₃ | CH₃ | p-Cl | " | CH₃ | J | 114 |
| 8 | H | H | 4 | CH₃ | CH₃ | p-Cl | N-piperazine-N—CH₃ | CH₃ | Cl | 139 |
| 9 | 2-Cl | H | 4 | H | H | p-Cl | NHCH₂CH₂N(C₂H₅)₂ | — | — | 133 |
|   |   |   |   |   |   |   |   | H | Citrate | 124 |
| 10 | 2-Cl | H | 4 | H | H | p-Cl | " | CH₃ | J | 229 |
| 11 | 2-Cl | H | 4 | H | H | p-Cl | " | CH₃ | Cl | 117 |
| 12 | H | H | 2 | H | H | p-Cl | " | C₆H₅CH=CH—CH₂ | Br | 182 |
| 13 | H | H | 4 | H | H | p-Cl | " | — | — | 168 |
|   |   |   |   |   |   |   |   | H | Citrate | 127 |
| 14 | H | 4-Cl | 3 | H | H | p-Cl | " | — | — | 170 |
|   |   |   |   |   |   |   |   | H | Citrate | 148 |
| 15 | 2-OH | H | 5 | H | H | p-Cl | " | — | — | 120 |
| 16 | 2-OCOCH₃ | H | 5 | H | H | p-Cl | " | — | — | 127 |
| 17 | 2-OCH₃ | H | 5 | H | H | p-Cl | " | — | — | 148 |
| 18 | H | H | 4 | H | H | p-J | " | — | — | 166 |
|   |   |   |   |   |   |   |   | H | Cl | 136 |
| 19 | H | H | 4 | H | H | p-Br | " | — | — | 166 |
|   |   |   |   |   |   |   |   | H | Citrate | 124 |
| 20 | H | H | 4 | H | OC₆H₄—p-Cl | p-Cl | " | — | — | 182 |
|   |   |   |   |   |   |   |   | H | Citrate | 155 |
| 21 | H | H | 4 | H | H | m-Cl | " | — | — | 100 |
| 22 | H | H | 4 | H | H | p-F | " | — | — | 150 |
|   |   |   |   |   |   |   |   | H | Cl | 131 |
| 23 | H | H | 4 | H | H | p-F | " | CH₂CH₂CH₂CH₃ | Br | 143 |
| 24 | H | H | 4 | H | H | m-CF₃ | " | — | — | 130 |
|   |   |   |   |   |   |   |   | H | Cl | 195 |
| 25 | H | H | 4 | H | H | o-Cl | " | — | — | 174 |
|   |   |   |   |   |   |   |   | H | Citrate | 124 |
| 26 | 5-Cl | H | 2 | H | H | p-Cl | " | — | — | 140 |
|   |   |   |   |   |   |   |   | H | Citrate | 134 |
|   |   |   |   |   |   |   |   | H | Fumarate | 15 |
| 27 | 5-Cl | H | 2 | H | H | p-Cl | " | CH₃ | J | 216 |
| 28 | 2-OCOCH₃ | H | 4 | H | H | p-Cl | " | — | — | 234 |
| 29 | 2-OH | H | 4 | H | H | p-Cl | " | — | — | 164 |
| 30 | 2-OH | H | 4 | H | H | p-Cl | " | CH₃ | J | 158 |
| 31 | 2-OCH₂ | H | 4 | H | H | p-Cl | " | — | — | 192 |
| 32 | 4-OCH₃ | H | 3 | H | H | p-Cl | " | — | — | 184 |
|   |   |   |   |   |   |   |   | H | Cl | 184 |
| 33 | 4-OCH₃ | H | 3 | H | H | p-Cl | " | CH₃ | J | 211 |
| 34 | H | H | 4 | CH₃ | H | p-Cl | " | — | — | 135 |
|   |   |   |   |   |   |   |   | H | Citrate | 151 |
| 35 | H | H | 4 | H | CH₃ | p-Cl | " | C₆H₅CH=CHCH₂ | Br | 117 |
| 36 | H | H | 3 | CH₃ | H | p-Cl | " | — | — | 141 |
|   |   |   |   |   |   |   |   | H | Cl | 155 |
| 37 | H | H | 3 | CH₃ | H | p-Cl | " | CH₃ | J | 139 |
| 38 | H | H | 2 | CH₃ | H | p-Cl | " | — | — | oily |
|   |   |   |   |   |   |   |   | H | Cl | 171 |
| 39 | 5-Cl | H | 2 | CH₃ | H | p-Cl | " | — | — | oily |
|   |   |   |   |   |   |   |   | H | Cl | 146 |
| 40 | 2-Cl | H | 4 | CH₃ | H | p-Cl | " | CH₃ | J | 55 (sint.) |
| 41 | H | 5-SO₂NH₂ | 2 | CH₃ | CH₃ | p-Cl | " | — | — | 120 |
| 42 | H | 5-SO₂NH₂ | 2 | CH₃ | CH₃ | p-Cl | NCH₂CH₂N(C₂H₅)₂ | C₂H₅ | J | 173 |
| 43 | H | H | 4 | CH₃ | CH₃ | p-Cl | " | — | — | 162 |

-continued

| Ex. | R$_1$ | R$_2$ | NH—Y in Position No. | R$_3$ | R$_4$ | Z | $\underset{N-X-N}{\overset{R_5}{\mid}}\underset{R_7}{\overset{R_6}{}}$ | R$_8$ | Acid Radical n=1 | MP °C |
|---|---|---|---|---|---|---|---|---|---|---|
| | | | | | | | | H | A$^1$ | 128 |
| | | | | | | | | H | A$^2$ | 52 |
| | | | | | | | | H | Nicotinate | 291 |
| 44 | H | H | 3 | CH$_3$ | CH$_3$ | p-Cl | " | — | — | oily |
| | | | | | | | | H | Cl | 146 |
| 45 | 5-Cl | H | 2 | CH$_3$ | CH$_3$ | p-Cl | " | — | — | oily |
| | | | | | | | | H | Cl | 167 |
| 46 | 2-Cl | H | 4 | CH$_3$ | CH$_3$ | p-Cl | " | — | — | 116 |
| | | | | | | | | H | Cl | 160 |
| | | | | | | | | H | Citrate | 122 |
| 47 | 4-OCH$_3$ | H | 3 | CH$_3$ | CH$_3$ | p-Cl | " | — | — | 79 |
| | | | | | | | | H | Cl | 160 |
| 48 | 2-Cl | H | 5 | CH$_3$ | CH$_3$ | p-Cl | " | — | — | 103 |
| | | | | | | | NHCH$_2$CH$_2$N$\underset{C_2H_5}{\overset{C_2H_5}{}}$ | H | Cl | 175 |
| 49 | 2-OCOCH$_3$ | H | 4 | CH$_3$ | CH$_3$ | p-Cl | " | — | — | oily |
| 50 | 2-OH | H | 4 | CH$_3$ | CH$_3$ | p-Cl | " | — | — | oily |
| 51 | 2-OH | H | 4 | CH$_3$ | CH$_3$ | p-Cl | " | CH$_3$ | J | 124 |
| 52 | 2-Cl | H | 5 | H | H | p-Cl | " | — | — | 131 |
| | | | | | | | | H | Cl | 228 |
| 53 | 2-Cl | H | 5 | H | H | p-Cl | " | C$_2$H$_5$ | J | 110 |
| 54 | H | 5-SO$_2$NH$_2$ | 2 | CH$_3$ | CH$_3$ | p-Cl | NHCH$_2$-pyrrolidine-N-C$_2$H$_5$ | — | — | 172 |
| 55 | H | 5-SO$_2$NH$_2$ | 2 | CH$_3$ | CH$_3$ | p-Cl | " | CH$_3$ | J | 124 |
| 56 | 5-Cl | H | 2 | CH$_3$ | H | p-Cl | " | — | — | oily |
| | | | | | | | | H | Cl | 145 |
| 57 | H | H | 4 | H | H | p-Cl | " | — | — | 117 |
| | | | | | | | | H | Cl | 126 |
| 58 | H | H | 4 | H | H | p-Cl | " | CH$_3$ | J | 63 |
| | | | | | | | NH—CH$_2$-pyrrolidine-N-C$_2$H$_5$ | | | |
| 59 | H | H | 2 | H | H | p-Cl | " | — | — | 129 |
| 60 | 2-Cl | H | 5 | H | H | p-Cl | " | — | — | 123 |
| | | | | | | | | H | Cl | 110 |
| 61 | 5-Cl | H | 2 | H | H | p-Cl | " | — | — | 166 |
| | | | | | | | | H | Cl | 194 |
| 62 | 2-OCOCH$_3$ | H | 4 | H | H | p-Cl | " | — | — | 168 |
| 63 | 2-OH | H | 4 | H | H | p-Cl | " | — | — | 183 |
| 64 | 4-OCH$_3$ | H | 3 | H | H | p-Cl | " | — | — | 186 |
| | | | | | | | | H | Cl | 196 |
| 65 | H | H | 4 | H | CH$_3$ | p-Cl | " | — | — | 137 |
| | | | | | | | | H | Citrate | 160 |
| 66 | H | 4-Cl | 3 | CH$_3$ | H | p-Cl | " | — | — | — |
| 67 | 2-Cl | H | 4 | H | CH$_3$ | p-Cl | " | — | — | oily |
| | | | | | | | NHCH$_2$-pyrrolidine-N-C$_2$H$_5$ | | | |
| 68 | H | H | 2 | H | CH$_3$ | p-Cl | " | — | — | 130 |
| 69 | H | H | 2 | H | CH$_3$ | p-Cl | " | C$_2$H$_5$ | J | 135 |
| 70 | 4-OCH$_3$ | H | 3 | CH$_3$ | CH$_3$ | p-Cl | " | — | — | oily |
| | | | | | | | | H | Cl | 137 |
| 71 | 2-Cl | H | 5 | CH$_3$ | CH$_3$ | p-Cl | " | — | — | 108 |
| | | | | | | | | H | Cl | 200 |
| 72 | 2-OCOCH$_3$ | H | 4 | CH$_3$ | CH$_3$ | p-Cl | " | — | — | oily |
| 73 | 2-OH | H | 4 | CH$_3$ | CH$_3$ | p-Cl | " | — | — | oily |
| 74 | 2-OH | H | 4 | CH$_3$ | CH$_3$ | p-Cl | " | CH$_3$ | J | 217 |
| 75 | H | H | 4 | CH$_3$ | CH$_3$ | p-Cl | " | — | — | 142 |
| | | | | | | | | H | Cl | 58 |
| | | | | | | | | H | Citrate | 73 |
| 76 | H | H | 3 | CH$_3$ | CH$_3$ | p-Cl | " | — | — | oily |
| | | | | | | | | H | Cl | 153 |
| 77 | H | H | 2 | CH$_3$ | CH$_3$ | p-Cl | " | — | — | 104 |
| 78 | 5-Cl | H | 2 | CH$_3$ | CH$_3$ | p-Cl | " | — | — | 94 |
| | | | | | | | | H | Cl | 234 |

-continued

| Ex. | R$_1$ | R$_2$ | NH—Y in Position No. | R$_3$ | R$_4$ | Z | $\underset{R_7}{\overset{R_5}{\underset{|}{N-X-N}}}\!\!-\!\!R_6$ | R$_8$ | Acid Radical n=1 | MP °C. |
|---|---|---|---|---|---|---|---|---|---|---|
| 79 | H | H | 4 | H | H | p-Cl | N⌒N—Y | — | — | 264 |
| 80 | H | H | 4 | H | H | m-CF$_3$ | " | — | — | 218 |
| 81 | H | H | 4 | H | H | o-Cl | " | — | — | 283 |
| 82 | H | H | 4 | CH$_3$ | H | p-Cl | " | — | — | 198 |
| 83 | H | H | 4 | CH$_3$ | CH$_3$ | p-Cl | " | — | — | 256 |
| 84 | 2-Cl | H | 4 | H | H | p-Cl | NHCH$_2$-pyridyl | — | — | 150 |
| 85 | H | 4-Cl | 3 | H | H | p-Cl | " | — | — | 212 |
|  |  |  |  |  |  |  |  | H | Cl | 222 |
| 86 | H | H | 4 | CH$_3$ | CH$_3$ | p-Cl | " | — | — | 185 |
|  |  |  |  |  |  |  |  | H | Cl | 143 |
| 87 | H | H | 4 | CH$_3$ | CH$_3$ | p-Cl | N⌒N—H | — | — | 130 |
|  |  |  |  |  |  |  |  | H | Cl | 294 |
| 88 | H | H | 4 | CH$_3$ | CH$_3$ | p-Cl | N⌒N—CHO | — | — | 137 |
| 89 | H | H | 4 | CH$_3$ | CH$_3$ | p-Cl | N⌒N—CH$_3$ | — | — | 128 |
|  |  |  |  |  |  |  |  | H | Cl | 240 |
|  |  |  |  |  |  |  |  | H | A$^2$ | 95 |
| 90 | H | H | 4 | CH$_3$ | CH$_3$ | p-Cl | NHCH$_2$CH$_2$—N(pyrrolidinyl) | — | — | 129 |
|  |  |  |  |  |  |  |  | H | Cl | 193 |
|  |  |  |  |  |  |  |  | H | Tartrate | 66 |
| 91 | 4-OCH$_3$ | H | 3 | H | H | p-Cl | NHCH$_2$CH$_2$—N(pyrrolidinyl) | — | — | 176 |
| 92 | H | H | 4 | CH$_3$ | CH$_3$ | p-Cl | NHCH$_2$CH$_2$CH$_2$N(C$_2$H$_5$)$_2$ | — | — | 144 |
|  |  |  |  |  |  |  |  | H | Citrate | 78 |

A$^1$: OOCC(CH$_3$)$_2$—OC$_6$H$_4$—pCl

A$^2$: OOC—C$_6$H$_4$—NHCOC(CH$_3$)$_2$—OC$_6$H$_4$—pCl

The preparation of ring-closed compounds according to general formula (III) is described in the following examples. All additional compounds prepared according to the method described herein are included in the tables listed hereinafter.

EXAMPLE 93

5.0 g (0.014 mol) 2-(p-chlorophenoxyacetamido)-4-chlorobenzoyl chloride are admixed in 100 ml chloroform with 1.7 g (0.014 mol) 2-diethylaminoethyl amine and heated under reflux for 8 hours. After cooling, the formulation is rinsed with diluted soda lye and water, and the solvent is removed by distillation under vacuum. The remaining residue is crystallized from diisopropyl ether, with a yield of 3.3 g (53.7%) 2-(p-chlorophenoxymethyl)-3-(2-diethylaminoethyl)-7-chloro-4 (3H)-quinazolinone with a MP of 104° C.

| Elementary Analysis: | | C | H | N |
|---|---|---|---|---|
| C$_{21}$H$_{23}$Cl$_2$N$_3$O$_2$ | (420.4) | Calculated: 59.99 | 5.52 | 9.99 |
| | | Found: 59.88 | 5.32 | 10.16 |

Hydrochloride MP 188° C.

EXAMPLE 94

8.1 g (0.02 mol) of the base according to example 4 with an MP of 109° C. are heated dry in a reaction vessel for 15 minutes to 180°–200° C., with the water formed in the process being sucked off by a weak vacuum applied close to the end of the reaction period. After cooling, the melt is crystallized from diisopropyl ether with a yield of 7.05 g (91.4%) 2-(p-chlorophenoxymethyl)-3-(2-diethylaminoethyl)-4-(3H)-quinazolinon with a MP of 85° C.

| Elementary Analysis: | | C | H | N |
|---|---|---|---|---|
| C$_{21}$H$_{24}$ClN$_3$O$_2$ | (385.9) | Calculated: 65.36 | 6.26 | 10.89 |
| | | Found: 64.72 | 6.25 | 10.72 |

Hydrochloride MP 194° C.

| Example | R1 | R2 | R3 | R4 | Z | X—N(R6)(R7) | R8 | Acid Radical n=1 | MP °C |
|---|---|---|---|---|---|---|---|---|---|
| 93 | Cl | H | H | H | p-Cl | CH₂CH₂N(C₂H₅)(C₂H₅) | — | — | 104 |
|   |   |   |   |   |   |   | H | Cl | 188 |
| 94 | H | H | H | H | p-Cl | " | — | — | 85 |
|   |   |   |   |   |   |   | H | Cl | 194 |
| 95 | Cl | H | H | H | p-Cl | " | CH₃ | J | 171 |
| 96 | H | H | H | H | p-Cl | " | CH₃ | J | 100 |
| 97 | H | H | H | CH₃ | p-Cl | " | H | Cl | 180 |
| 98 | H | Cl | H | H | p-Cl | " | — | — | 158 |
|   |   |   |   |   |   |   | H | Citrate | 141 |
| 99 | H | SO₂NH₂ | H | H | P-Cl | " | — | — | 207 |
| 100 | H | H | CH₃ | H | p-Cl | " | — | — | oily |
| 101 | H | SO₂NH₂ | H | H | p-Cl | " | — | — | 210 |
| 102 | H | H | H | CH₃ | p-Cl | CH₂—(N-pyrrolidinyl-C₂H₅) | — | — | oily |
| 103 | H | H | H | H | p-Cl | " | — | — | oily |
|   |   |   |   |   |   |   | H | Cl | 140 |
| 104 | H | Cl | H | H | p-Cl | " | — | — | 297 |
|   |   |   |   |   |   |   | H | Cl | 137 |
| 105 | H | Cl | H | H | p-Cl | CH₂—(2-pyridyl) | — | — | 114 |
|   |   |   |   |   |   |   | H | H | 238 |

We claim:

1. Aminobenzoic acid compounds of the formula:

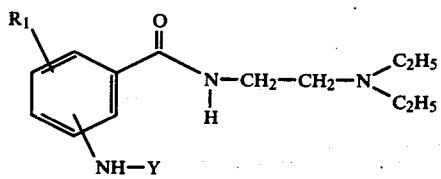

wherein R₁ is hydrogen, chlorine, hydroxy, acetoxy or C₁–C₃-alkoxy; Y is the group:

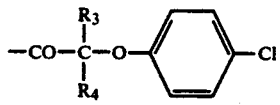

wherein R₃ and R₄ are hydrogen or methyl and their acid addition salts.

2. A pharmaceutical composition having a lipid-lowering and antiarrhythmic activity comprising an effective lipid-lowering and antiarrhythmic amount of a compound as defined in claim 1 and a pharmaceutically acceptable carrier therefor.

* * * * *